United States Patent [19]
Liu

[11] Patent Number: 5,130,092
[45] Date of Patent: Jul. 14, 1992

[54] BIOLOGICAL WASTE STERILIZATION AND FUEL PRODUCT THEREFROM

[76] Inventor: Hsin Liu, 40-25 Hampton St., Elmhurst, N.Y. 11373

[21] Appl. No.: 564,848

[22] Filed: Aug. 8, 1990

[51] Int. Cl.[5] .......................... A61L 2/04; C10L 1/00
[52] U.S. Cl. ........................................ 422/28; 44/543; 44/545; 44/605; 44/606; 44/628; 44/307; 208/15; 241/16; 241/17; 241/23; 241/DIG. 38; 422/32; 422/38; 585/13; 585/14; 585/240
[58] Field of Search ............... 422/28, 32, 38; 208/15; 585/13, 14, 240; 44/90, 61, 543, 545, 605, 606; 241/16, 17, 23, DIG. 38

[56] References Cited

U.S. PATENT DOCUMENTS

| | | | |
|---|---|---|---|
| 2,294,087 | 8/1942 | Johnson | 422/300 |
| 2,731,208 | 1/1956 | Dodd | 422/28 |
| 2,786,245 | 3/1957 | Steinbock, Jr. | 422/301 |
| 2,806,123 | 9/1957 | Steinbock, Jr. | |
| 3,579,290 | 5/1971 | Pickstone | |
| 3,951,731 | 4/1976 | Jetzer | 241/DIG. 38 |
| 4,089,773 | 5/1978 | Espenscheid | 585/240 |
| 4,145,188 | 3/1979 | Espenscheid et al. | 585/240 |
| 4,266,083 | 5/1981 | Huang | 585/240 |
| 4,374,491 | 2/1983 | Stortroen et al. | |
| 4,552,720 | 11/1985 | Baker, Sr. et al. | 422/26 |
| 4,618,735 | 10/1986 | Bridle et al. | 585/240 |
| 4,644,586 | 2/1987 | Padgett | |
| 4,800,015 | 1/1989 | Simmons | |

FOREIGN PATENT DOCUMENTS 0277507 1/1987 European Pat. Off.
355564 11/1905 France.

Primary Examiner—Robert J. Warden
Assistant Examiner—Timothy M. McMahon
Attorney, Agent, or Firm—Rosen, Dainow & Jacobs

[57] ABSTRACT

A process for sterilizing biological waste such as medical waste and a biomass fuel product from sterilized waste are disclosed. The biological waste preferably includes waste capable of sorbing substantial amounts of a liquid fuel having a boiling temperature higher than about 240° F. The waste is shredded and then introduced into a container holding the liquid fuel, which is maintained at atmospheric pressure at a temperature between about 240° F. and the boiling temperature of the liquid fuel. The shredded waste is immersed in the liquid fuel for a time sufficient to effect sterilization of the shredded waste. Thereafter, the sterilized shredded waste is removed from the container, and ground to either make it pumpable or increase its pumpability, and to further destroy the physical shape of the waste as to make it unrecognizable. The ground waste is then pumped to a desired location. The waste with sorbed liquid fuel is atomizable and usable as a fuel for many applications.

37 Claims, 1 Drawing Sheet

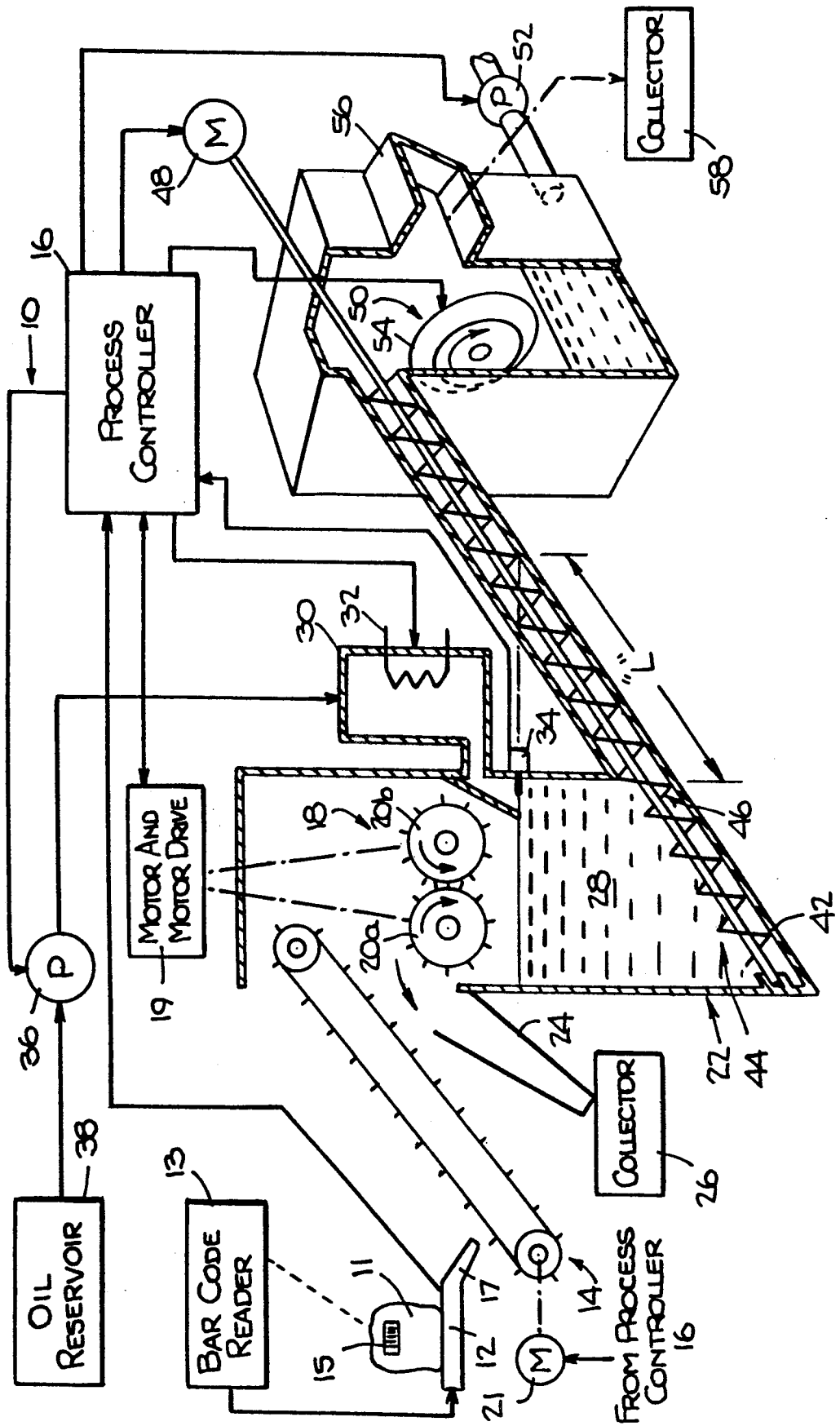

BIOLOGICAL WASTE STERILIZATION AND FUEL PRODUCT THEREFROM

BACKGROUND OF THE INVENTION

The invention relates generally to safely disposing of biologically-contaminated material, and more particularly to a method for sterilizing biological waste, e.g., medical and/or infectious waste. The invention also relates to disposing of the sterilized biological waste, and to a biomass fuel product made from the waste.

As used herein, "biological waste" has a broad meaning and includes refuse, garbage, waste, etc. that is or is perceived to be capable of transmitting disease rather readily, and biological materials considered to be hazardous to humans or to selected living matter, e.g., refuse, garbage, waste, or other material that contains infectious or other microorganisms. Biological waste thus includes medical and infectious wastes, but would exclude industrial garbage and refuse.

The management, handling and disposal of biological waste has become a matter of increasing concern in recent years both to the public, to health care providers and to medical, research and biological laboratories. Nationally, hospitals are the major generators of medical waste, producing in excess of 500,000 tons each year in the United States. Many states concerned with the growing threat of Acquired Immune Deficiency Syndrome (AIDS) have caused more and more articles and materials to come under the definition of medical waste, which is expected to more than double the amount of medical waste being generated. The health and environmental dangers posed by biological waste mandate that special collection, transportation and disposal techniques be developed.

Hospitals, doctors offices, dentists offices, laboratories, nursing homes, funeral homes and private residences are all legally liable for the safe and effective disposal of medical waste.

The federal Medical Waste Tracking Act of 1988 (Public Law 100-82, Nov. 1, 1988, 102 Stat. 2950) established standards for the tracking and management of all medical waste including the following: cultures and stocks of infectious agents; human blood and blood products; human pathological waste, including those from surgery and autopsy; contaminated animal carcasses from medical research; waste from patients isolated with highly communicable diseases; and all used sharp implements, such as needles and scalpels, as well as certain unused sharp objects in facilities of the type described above.

Sterilization of biological waste is a safe, cheap and practical method of solid waste management and disposal, which avoids the environmental costs of incineration and which limits public exposure to biologically hazardous materials.

Conventional waste sterilization processes are typically batch processes and typically employ either dry heat or steam and a pressurized container. Such processes typically require that the waste remain at least one hour in the pressurized container to complete a batch cycle. Those processes have the disadvantage of high capital and operating costs due to high pressure operation, particularly for the construction and operation of a high pressure vessel large enough to provide a high batch throughput. Other waste sterilization processes employ radiation and/or various chemical agents; these processes have the disadvantage that they generate secondary environmental problems. Still another waste sterilization process employs microwave heating of the biological waste; this process has the disadvantage of high capital and operating costs.

SUMMARY AND OBJECTS OF THE INVENTION

It is an object of the invention disclosed herein to facilitate disposal of biological waste, particularly medical waste.

It is another object of the invention to sterilize and dispose of biological waste, particularly medical waste, while reducing waste disposal responsibilities, limiting public exposure to the waste and protecting the environment and atmosphere.

It is another object of the invention to provide an improved process for sterilizing biological waste, particularly medical waste.

It is another object of the invention to provide a process for sterilizing biological waste, particularly medical waste, which so physically alters or destroys the shape of the material being sterilized that such material is not reusable, and is rendered unrecognizable as the original material.

It is another object of the invention to sterilize biological waste, particularly medical waste, without discharging pollutants into the environment or atmosphere.

It is another object of the invention to provide an improved, commercially viable, high speed, continuous process for sterilizing biological waste, particularly medical waste.

It is another object of the invention to provide a process for sterilizing biological waste, particularly medical waste, in which the waste after sterilization can be transported, stored and handled by conventional material handling equipment and personnel.

It is another object of the invention to provide a process for sterilizing biological waste that provides a sterilized waste product usable as a biomass fuel; it is another object to provide such a process which utilizes potential pollutants to increase the fuel content of the sterilized waste.

It is another object of the invention to provide a biomass fuel product from biological waste.

Briefly, the invention achieves various of these objects and other objects by immersing biological waste in a high boiling temperature liquid heated to at least 240° F. at about atmospheric pressure, for a time sufficient to effect sterilization of the waste material. In a preferred embodiment, the biological waste is sterilized in a continuous process at atmospheric pressure, i.e., the process is operated substantially continuously at atmospheric pressure with waste being introduced into and removed from the liquid while the process is sterilizing waste immersed in the liquid.

Unless otherwise indicated, temperatures including boiling temperatures are at one atmosphere pressure (also referred to as at atmospheric pressure).

The temperature and level of the high boiling temperature fluid are preferably controlled, as preferably is the introduction of waste into the liquid, in order to ensure that the waste is sterilized without remaining in the liquid longer than necessary. This maximizes the throughput of the continuous process.

In an embodiment of the invention, biological waste including substantial amounts of sorbent material (i.e., absorbent and/or absorbent material) is sterilized in a high boiling temperature liquid which is a combustible fuel, such as oil. During sterilization, such sorbent material sorbs (i.e., adsorbs and/or absorbs) a sufficient quantity of the high boiling temperature liquid while immersed therein to provide sterilized waste having a sufficiently high fuel content to be usable as a fuel.

Preferably, the waste either retains an amount of moisture and/or sorbs an amount of the high boiling temperature liquid so that the waste is pumpable and/or transportable by convention material handling equipment, and is preferably atomizable by conventional fuel atomizers.

Preferably, the biological waste is treated (e.g., by shredding and/or grinding) before and/or after sterilization. Such treatment either makes the waste pumpable or increases its pumpability. Also such treatment so physically alters or destroys the shape of the material being sterilized that such material is not reusable, and is rendered unrecognizable as the original material. Preferably, such treatment enables the waste to be pumped as a liquid fuel, and atomized as a liquid fuel.

In a process according to an embodiment of the invention, the waste is weighed and then shred into small pieces prior to introducing the waste into the high boiling temperature liquid, which is preferably No. 6 fuel oil. Non-shreddable material is separated by the shredder and handled as non-sterilized material. The shredded waste is then introduced in a substantially continuous manner into a container or vessel containing the high boiling temperature liquid which is heated to and maintained at between about 240° F. and the boiling temperature of the liquid at about atmospheric pressure. The shredded waste is immersed in the high boiling temperature liquid for a time sufficient to effect sterilization of the waste material. The high boiling temperature liquid is replenished as necessary, preferably without stopping the process. Preferably, the waste moves in the container from its point of entry therein to a location from which it is removed from the container. After the waste has been immersed in the high boiling temperature liquid for a given time, it is removed, also in a continuous fashion. The sterilized waste, which has a substantial moisture and/or high boiling temperature liquid content, is then ground and pumped to a location for storage or transporting.

A continuous process for sterilizing medical waste including sorbent waste capable of sorbing a substantial amount of a liquid fuel while immersed therein, according to the invention, comprises shredding the waste; introducing into and immersing shredded waste in a liquid fuel having a boiling temperature higher than about 240° F. at atmospheric pressure for a time sufficient to effect sterilization of the waste; maintaining the liquid fuel at a substantially constant temperature of between 240° F. and the boiling temperature of the liquid fuel; removing sterilized waste from the liquid fuel; and grinding the sterilized waste. Either or both the shredding or the grinding being effective to either make the sterilized waste pumpable or to increase its pumpability.

In the preferred embodiment, the shredded waste is introduced into the top of the container and gradually falls to the bottom thereof where it is removed from the container by a screw apparatus and delivered to a grinder. The screw conveyor has an input end located in or adjacent the bottom of container and a discharge end feeding the grinder. Part of the conveyer of length "L" is filled with the high temperature liquid. The conveyer has a linear speed "V". The retention time "t" of waste immersed in the high temperature liquid in the length "L" of the screw conveyor is calculated to be sufficient to sterilize the waste at the temperature of the high boiling point liquid for the particular waste being sterilized. The speed "V" and the length "L" are selected according to the equation $L/V = t$, where "t" is long enough to sterilize the waste.

Non-grindable materials waste material such as metal and glass articles are rejected by the grinder and collected separately. Such sterilized articles may be disposed of in the same way as ordinary solid refuse.

According to the invention, a pumpable fuel product is provided comprising sterilized biological waste and at least about 15% by weight and up to about 25% by weight liquid fuel.

The above and other objects, aspects, features and advantages of the invention will be more readily perceived from the description of the preferred embodiments thereof taken in conjunction with the accompanying drawing and appended claims.

BRIEF DESCRIPTION OF THE DRAWING

A process according to the invention is illustrated by way of example and not limitation in the sole figure of the accompanying drawing which is a schematic diagram of apparatus for carrying out the process. It will be understood that the invention is not limited to the embodiment described and that the drawing is for purposes of illustration only and is not intended as a definition of the limits of the invention.

DESCRIPTION OF THE PREFERRED EMBODIMENTS

In the preferred embodiment, the process employs a combustible liquid fuel, such as oil, as the high boiling temperature liquid, and sterilizes medical wastes which include substantial amounts of oil-sorbent waste material (such as paper, fabric material, wound dressing material, tissue, etc.) which when immersed in the heated liquid fuel sorb substantial amounts of the fuel. The medical waste may also include non-sorbent material or articles such as glass, metal, and plastic articles.

Referring to the drawing, the system 10 sterilizes medical waste 11 deposited (preferably in sealed plastic bags) on a scale 12 located at the input end of a belt conveyer 14 with flights to lift the waste 11. In accordance with current handling procedures, the sealed plastic bags containing the medical waste 11 may have a bar code thereon, for example, for waste accountability and tracking, and also for customer billing purposes. A bar code reader 13 may be provided at the scale location for reading the bar code. Scale 12 may be computerized and incorporate bar code reader 13. The bar code may be contained on a label 15 attached to the bag. Bar code information read from such a label is associated with weight information provided by scale 12, and possibly other information such as the location of the sterilization system 10, time of day, etc. Such information may be transmitted to a desired computer or other equipment and to a process controller 16 for process control purposes.

From scale 12, the waste is deposited on conveyer 14 (for example manually or automatically by pushing the bags onto chute 17) which delivers the bagged waste 11 to high torque shredder 18. Conveyor 14 is driven by motor 21 under control of controller 16. Shredder 18 shreds and crushes the waste to a maximum particle size which passes 0.25 inch screen. The minimum particle size passes 100 mesh. Preferably, the average particle size is about 0.125 inch. Shredder 18 is a conventional shredder having tool steel hammers to shred all of waste 11 except articles such as metal instruments. Thus, syringes, soft material, etc. are shredded. Non-shreddable items such as metal instruments are rejected by shredder 18, as follows. Shredder motor and motor drive 19 drives both shredder rollers 20a and 20b towards each other to shred shreddable material therebetween, which is dropped into container 22. When a non-shreddable item becomes lodged between rollers 20a and 20b, that item is detected by process controller 16 (e.g. by a sensor, not shown, or by changes detected in motor and motor drive 19). Controller 16 then via motor and motor drive 19 causes the left roller 20a to reverse and the right roller 20b to be stationary. Left roller 20a then moves the item from shredder 18 onto chute 24 where it drops into collector into 26. Since such items have not been sterilized, they are handled accordingly. The number of such non-shreddable items is expected to be very small.

Shredder 18 is disposed above liquid fuel container 22 so that waste 11 shredded by shredder 18 is ejected or falls into the top of container 22. Container 22 holds a combustible liquid fuel 28 therein having a boiling temperature higher than 240° F. at atmospheric pressure. Liquid fuel 28 is introduced into container 20 from a fuel heating tank 30 in which liquid fuel is heated by heater 32 under control of controller 16 to a temperature sufficiently above 240° F. to ensure a minimum temperature of 240° F. in container 22 while waste is being sterilized therein. Depending on the size of container 22, it may be necessary to recycle liquid fuel through tank 30, or employ an auxiliary heater in container 22 to maintain a constant temperature of the liquid fuel in container 22 of at least 240° F. Preferably, the temperature of liquid fuel 28 in container 22 is maintained in the range of between about 240° F. and about 270° F. The waste 11 is maintained immersed in liquid fuel 28 for a time sufficient to sterilize it, as described below. Shredding the waste into smaller pieces advantageously decreases the required immersion time.

Container 22 holds 100 to 200 gallons of liquid fuel 22 below the normal volume level of liquid fuel 22 therein. The size of container 22 may be larger or smaller depending upon the particular application and the particular process parameters desired. A level control comprising level sensor 34 and process controller 16 is provided to automatically replenish liquid fuel 28 in container 22 to insure a minimum liquid fuel level in container 22. Process controller 16 selectively activates pump 36 to pump liquid fuel from a fuel reservoir 38 to fuel heating tank 30.

Waste 11 entering the top of container 22 relatively slowly falls by gravity to the bottom 42 of container 22 where it is removed by a screw conveyor 44. The input end 46 of screw conveyer 44 is disposed along the bottom 42 of container 22 to receive waste falling by gravity to the container bottom. Container bottom 42 is sloped upwardly at a suitable angle for conveyer 44 to lift waste upwardly. The liquid fuel level in container 22 is such that a length "L" of the conveyer contains liquid fuel through which the conveyer moves waste that has fallen to bottom 42 of container 22. Conveyer 44 is rotated at a linear speed "V" by a motor 48 under control of process controller 16.

The retention time "t" of the waste in liquid fuel 28 is determined by the length "L" and the conveyer speed "V" according to the equation $L/V = t$. The waste must be immersed in the liquid fuel for a period of time sufficient to effect complete sterilization. The precise temperature and time required to effect sterilization of the waste depends on the waste and may be determined in a bacteriology laboratory. This information may be supplied to process controller 16. The conveyer rotation speed may then be adjusted to maintain the waste submerged in the liquid fuel for the desired retention time. The minimum retention time is calculated based on movement of the waste by conveyer 44 along the length "L" while immersed in liquid fuel 28. Such minimum retention time does not, but may, include the time it takes for the waste to fall to the container bottom 42 and be moved by conveyer 44 into length "L". Process controller 16 allows automatic sterilization and collection of the waste.

Conveyer 44 lifts the waste from container 22 and deposits it in grinder 50 which grinds the waste into a pumpable slurry having a particle size less than about 50 mesh. Grinder 50 may be a conventional wood pulp grinder which grinds the waste to fine mesh size, in the range of 50 to 100 mesh. Shredding and/or grinding physically destroys the appearance and shape of the waste so that it cannot be reused and is rendered unrecognizable as the original waste. This additional grinding of the sterilized waste permits the waste to be easily pumped by a conventional pump 52 to a storage or transporting location. The slurry is of a consistency to permit atomization by conventional heavy fuel atomizers.

Centrifugal forces in grinder 50 separate non-grindables such as metal objects and glass which are thrown by high-speed rotating disc 54 into chute 56 and collected in collector 58. Such unground waste material rejected by the grinder 50 is thereby separated from the ground waste and disposed of as ordinary refuse. Thus, the unground waste become solid waste; and since it has been sterilized, it poses no health or environmental threat.

During the time that the waste 11 is immersed in liquid fuel 28, the waste sorbs a substantial amount of liquid fuel so that with such sorbed liquid fuel and any moisture retained by the waste, the waste is pumpable by conventional pump 52.

The period of time that the waste is immersed in the liquid fuel, i.e., the time required for sterilization, depends on a number of factors, including the temperature at which the liquid fuel is heated, the volume of the waste to be treated and the nature of the waste, which may vary by location and source. The precise temperature and time required to effect sterilization of waste from a particular location and source may be measured and calculated in a bacteriology laboratory. As the temperature of the liquid fuel is increased, the required immersion time to achieve sterilization may be decreased. However, the temperature must be maintained at a minimum of at least 240° F. While a smaller volume of waste will require less time for sterilization, the average immersion time is in the range of about 15 to about 40 minutes. The total processing time for 10,000 pounds of hospital waste from weigh-in to exit from the system 10 is in the range of approximately 10 to 20 hours.

System 10 may be automated under control of process controller 16, or system 10 may be manually monitored and manually controlled using manually activated controls for the various motors, the heater, etc. Process controller 16 may comprise conventional process control circuitry and may include a microcomputer or microcontroller. Such circuits are known to those of skill in the art and may be programmed in accordance with the process disclosure herein.

The liquid fuel may be any not previously used or previously used or waste oil, such as petroleum oil (e.g., heavy or light fuel oil, crude oil), mineral oil or vegetable oil, having a boiling temperature substantially above about 240° F., e.g., at or above about 270° F., may be used as the liquid fuel. Use of a heavier weight oil such as No. 6 fuel oil (specific gravity=0.986) improves storageability. Lighter oils such as No. 2 fuel oil or corn oil are much less denser than the waste and water so that over time a separation of the oil from the waste and or the water occurs. Such separation does not readily occur when the density of the oil is close to that of the waste and that of water. If a lighter density oil is used, such as No. 2 oil or corn oil, a colloidal agent, such as magnesium oxide, may be added to prevent the separation of water and oil.

No. 6 fuel oil which has a boiling temperature higher than 300° F. at atmospheric pressure (about 350° F.), as mentioned above, is preferred. Preferably, heated No. 6 oil is maintained at a constant temperature of 270° F. at atmospheric pressure without boiling. Waste containing sorbed No. 6 fuel oil may be stored for up to at least 12 months, without substantial separation of oil from the waste.

During the sterilization process, a portion of the oil is sorbed by the sorbent portion of the waste, which is retained in the waste after the sterilized waste is conveyed out from the heated oil bath by the screw conveyor. The final waste product is thus a homogeneous, atomizable refuse slurry which may be used as a fuel source, as it comprises in the range of about 10 to about 25% by weight oil sorbed from container 22 and conveyer 44. The sterilized waste is an effective fuel for furnaces, power plant boilers, incinerators and the like.

The medical waste material 11 may have a substantial moisture content, e.g., 15% to 50% by weight, when it is introduced into container 22.

To provide a permanent record of biological waste from collection at a customer's site to sterilization, bar coding and a computer tracking system may be employed. The biological waste from a particular source may be collected in a separate colored bag, marked by bar coding to indicate date collected, weight, source, contents and other relevant information. The bar code may be read at any trans-shipment and storage location, when the waste is weighed prior to sterilization. This provides for tracking of the waste in compliance with law.

In compliance with most statutory requirements for safe disposal of medical waste, the invention advantageously provides for both biological sterilization and effective destruction of medical waste such that it is rendered unrecognizable. The shape of the waste material is physically destroyed by the shredding and grinding, so that the article is unidentifiable and cannot be reused. Additionally, when the sterilized and ground waste is finally burnt as a fuel source, the waste is finally and safely disposed of.

EXAMPLE 100 pounds of typical medical waste collected from a hospital in New York City was deposited on a belt conveyer and conveyed to a shredder, where it was shredded to an average size of about 0.25 inch. The shredded waste was then passed to a bath containing heated No. 6 fuel oil. The oil temperature was maintained at constant temperature of about 270° F. at atmospheric pressure. The medical waste was treated by retention and soaking in the heated oil bath for a minimum of 22 minutes until sterilization was effected. The oil-sorbed waste was then transferred by a screw conveyor from the heated oil bath to a grinder, where it was ground in the range of 50 to 100 mesh size. Metal, glass and other ungrindable materials or articles rejected by the grinder were transferred to a landfill. Non-shredded, unsterilized waste is treated as unsterilized waste. The sterilized waste was tested and found to be totally non-infectious. The sterilized medical waste had the following characteristics:

| | |
|---|---|
| Heating Value: | Minimum 10,000 BTU/lb. |
| Ash: | Maximum 22% |
| Sulfur: | Maximum 0.4% |
| Moisture: | Minimum 50% |
| Density: | Maximum 63.59 lb/Cu Ft. |
| Sabolt Viscosity (SSU at 100° F.): | Maximum 100 Minimum 35 |
| Pumpability (5 hp drive at 100° F.) | Minimum 180 gal/hr. Maximum 460 gal/hr. |
| Storageability | Minimum 12 months (without substantial separation of oil) (Remained disinfected) |

The invention is not intended to be limited to the preferred embodiment thereof described above or the Example described above, which are meant to be illustrative rather than exhaustive. Also, certain changes and modifications of the embodiments of the invention herein disclosed will be readily apparent to those of skill in the art. It is the applicant's intention to cover by the claims all such changes and modifications which could be made to the embodiments of the invention herein chosen for the purposes of disclosure which do not depart from the spirit and scope of the invention.

I claim:

1. A process for sterilizing biological waste comprising immersing said waste in liquid having a boiling temperature higher than 240° F. and maintained at a sterilizing temperature between about 240° F. and about 270° F. and below the boiling temperature of said liquid at atmospheric pressure for a time sufficient to sterilize said waste, and removing said waste from immersion in said liquid to provide said waste in a sterilized condition.

2. The process of claim 1 wherein said liquid is a fuel oil.

3. The process of claim 2 wherein said waste includes substantial amounts of waste which sorbs said fuel oil.

4. The sterilized waste product with sorbed fuel oil made according to the process of claim 3.

5. A continuous process for sterilizing biological waste comprising immersing said waste in a liquid having a boiling temperature higher than about 240° F., maintaining the temperature of the liquid at a sterilizing temperature between about 240° F. and about 270° F. and below the boiling temperature of said liquid, maintaining said waste immersed in said liquid for a time sufficient to sterilize said waste, and thereafter removing said waste from immersion in said liquid to provide said waste in a sterilized condition, said process being operated substantially continuously at atmospheric pressure with waste being introduced into and removed from said liquid while said process is sterilizing waste immersed in said liquid.

6. The process of claim 5 wherein said liquid is selected from the group consisting of petroleum oils, vegetable oils and mineral oils.

7. The process of claim 5 wherein said liquid is a fuel oil.

8. The process of claim 5 wherein said liquid is No. 6 fuel oil.

9. The process of claim 7 wherein said waste includes substantial amounts of waste which sorbs said fuel oil.

10. The sterilized waste product with sorbed fuel oil made according to the process of claim 9.

11. A process for sterilizing biological waste which includes substantial amounts of sorbent waste, comprising immersing said waste in a said liquid fuel having a boiling temperature higher than 240° F. heated to a sterilizing temperature between about 240° F. and about 270° F. and below the boiling temperature of said liquid fuel at atmospheric pressure for a time sufficient to sterilize said waste and for said waste to sorb an amount of said liquid fuel sufficient to increase the fuel content of said waste, and removing said waste from immersion in said liquid fuel.

12. The process of claim 11 wherein said liquid fuel is an oil.

13. The process of claim 11 wherein said liquid fuel is No. 6 fuel oil.

14. The sterilized waste product with sorbed liquid fuel made according to the process of claim 11.

15. A continuous process for sterilizing biological waste including sorbent waste capable of sorbing a substantial amount of a liquid while immersed therein, comprising:
  immersing shredded biological waste in a said liquid having a boiling temperature higher than about 240° F.;
  maintaining at atmospheric pressure said liquid at a substantially constant temperature between 240° F. and 270° F. and below the boiling temperature of said liquid while retaining said waste immersed in said liquid for a time sufficient to sterilize said waste;
  thereafter removing sterilized waste from said liquid; and
  treating said waste either prior to immersing it in said liquid or after it is removed from said liquid, or both, to either make said sterilized waste pumpable or to increase its pumpability.

16. The process of claim 15 wherein said liquid is held in a container having a top and a bottom, and said waste is introduced into said container from the top thereof and removed from the bottom thereof with a screw conveyer.

17. The process according to claim 16 wherein said screw conveyer includes a portion containing heated liquid, the speed of said conveyer, the length of said portion and the temperature of said liquid being such that waste moved through said conveyer portion is sterilized while immersed in liquid in said conveyer portion.

18. The process of claim 15 wherein said liquid is a fuel oil.

19. The sterilized waste product with sorbed liquid fuel oil made according to the process of claim 18.

20. A continuous process for sterilizing medical waste including sorbent waste capable of sorbing a substantial amount of a liquid fuel while immersed therein, comprising:
  shredding said waste;
  immersing shredded waste in a said liquid fuel having a boiling temperature higher than about 240° F.;
  maintaining at atmospheric pressure said liquid fuel at a substantially constant temperature between 240° F. and 270° F. and below the boiling temperature of said liquid fuel while retaining said waste immersed in said liquid fuel for a time sufficient to sterilize said waste;
  thereafter removing sterilized waste from said liquid fuel; and
  grinding said sterilized waste;
  either or both said shredding or said grinding being effective to either make said sterilized waste pumpable or to increase its pumpability.

21. The process of claim 22, wherein said liquid fuel is held in a container having a top and a bottom, and said waste is introduced into said container from the top thereof and removed from the bottom thereof with a screw conveyer.

22. The process of claim 21 wherein said screw conveyer includes a portion containing heated liquid fuel, the speed of said conveyer, the length of said portion and the temperature of said liquid fuel being such that waste moved through said conveyer portion is sterilized while immersed in liquid fuel in said conveyer portion.

23. The process of claim 22 including moving said waste after grinding thereof to a desired location by pumping.

24. The process of claim 22 wherein said liquid fuel is selected from the group consisting of petroleum oils, vegetable oils and mineral oils.

25. The process of claim 22 wherein said liquid fuel is No. 6 fuel oil.

26. The sterilized waste product with sorbed liquid fuel oil made according to the process of claim 22.

27. A process for sterilizing biological waste comprising:
  providing biological waste including waste capable of sorbing substantial amounts of a liquid fuel having a boiling temperature higher than about 240° F.;
  shredding said biological waste to provide shredded waste;
  introducing said shredded waste into a container holding said liquid fuel;
  maintaining said liquid fuel in said container at atmospheric pressure at a temperature between about 240° F. and about 270° F. and below the boiling temperature of said liquid fuel;
  maintaining said shredded waste immersed in said liquid fuel for a time sufficient to effect sterilization of said shredded waste;
  removing sterilized waste from said container; and
  grinding said sterilized waste;
  either or both said shredding or said grinding being effective to either make said sterilized waste pumpable or to increase its pumpability.

28. The process of claim 27 wherein said grinding is carried out in a wood pulp grinder which grinds grindable waste and separates non-grindable waste from the ground waste.

29. The process of claim 27 wherein said liquid fuel is introduced into the top of said container and removed from the bottom thereof with a screw conveyer.

30. The process of claim 29 wherein said screw conveyer includes a portion containing heated liquid fuel, the speed of said conveyer, the length of said portion and the temperature of said liquid fuel being such that waste moved through said conveyer portion is sterilized while immersed in liquid fuel in said conveyer portion.

31. The process of claim 27 including moving said waste after grinding thereof to a desired location by pumping.

32. The process of claim 27 wherein said liquid fuel is selected from the group consisting of petroleum oils, vegetable oils and mineral oils.

33. The process of claim 27 wherein said liquid fuel is No. 6 fuel oil.

34. The sterilized waste product with sorbed liquid fuel oil made according to the process of claim 27.

35. A process for sterilizing biological waste comprising immersing said waste in liquid having a boiling temperature higher than 270° F. and maintained at a sterilizing temperature between about 240° F. and 270° F. at atmospheric pressure for a time sufficient to sterilize said waste, and removing said waste from immersion in said liquid to provide said waste in a sterilized condition.

36. A process for sterilizing biological waste having a moisture content of from about 15% to about 50% by weight, comprising immersing said waste in liquid having a boiling temperature higher than 240° F., and maintaining said liquid at a sterilizing temperature at atmospheric pressure between about 240° F. and about 270° F. and below the boiling temperature of said liquid, maintaining said waste in said liquid for a time sufficient to sterilize said waste without substantially reducing the moisture content of said waste, and removing said waste from immersion in said liquid to provide said waste in a sterilized condition with a moisture content of from about 15% to about 50% by weight.

37. A process for sterilizing biological waste which includes substantial amounts of sorbent material capable of sorbing a substantial amount of a liquid fuel and has a moisture content of from about 15% to about 50% by weight, comprising immersing said waste in a said liquid fuel having a boiling temperature higher than 240° F., maintaining said liquid fuel at a sterilizing temperature at atmospheric pressure between about 240° F. and about 270° F. and below the boiling temperature of said liquid fuel, maintaining said waste in said liquid fuel for a time sufficient to sterilize said waste without substantially reducing the moisture content of said waste and for said waste to sorb an amount of said liquid fuel sufficient to substantially increase the fuel content of said waste, and removing said waste from immersion in said liquid fuel to provide said waste in a sterilized condition with a substantial amount of sorbed liquid fuel and with a moisture content of from about 15% to about 50% by weight.

* * * * *